United States Patent [19]
Delaunois et al.

[11] 3,946,083
[45] Mar. 23, 1976

[54] HALOGENATED AROMATIC ETHERS

[75] Inventors: Yvon Delaunois, Tessenderlo; Pierre Hestermans, Brussels; Georges Leroy, Brussels; Fernand Peerts, Heverlee; Claude Wilante, Brussels, all of Belgium

[73] Assignee: Tessenderlo Chemie S.A., Tessenderlo, Belgium

[22] Filed: Apr. 7, 1975

[21] Appl. No.: 565,713

[30] Foreign Application Priority Data
Apr. 10, 1974   France ............... 74.12537

[52] U.S. Cl. ............... 260/611 A; 252/54; 252/77; 252/65
[51] Int. Cl.² ............................ C07C 43/20
[58] Field of Search ................. 260/611 A

[56] References Cited
UNITED STATES PATENTS

| | | | |
|---|---|---|---|
| 2,397,799 | 8/1943 | Martin et al. ............ | 260/611 A X |
| 2,409,274 | 10/1946 | Hanford et al. .......... | 260/611 A X |
| 2,567,350 | 9/1951 | Rieveschl, Jr. .......... | 260/611 A |
| 2,794,054 | 5/1957 | Craig et al. ............. | 260/611 A |
| 2,847,477 | 8/1958 | Watanabe et al. ........ | 260/611 A |
| 3,060,242 | 10/1962 | Gordon .................... | 260/611 A |
| 3,544,557 | 12/1970 | Nauto et al. ............. | 260/611 A X |
| 3,565,955 | 2/1971 | Ehrhart et al. ........... | 260/611 A X |

*Primary Examiner*—Bernard Helfin
*Attorney, Agent, or Firm*—Millen, Raptes & White

[57] ABSTRACT

Suitable as lubricants or dielectric fluids are ethers of the formula

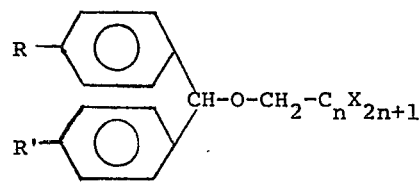

wherein X is F or H, at least one of the substituents X being F, $n$ is a whole number at least equal to 1, R and R' being identical or different represent H or Cl.

16 Claims, No Drawings

HALOGENATED AROMATIC ETHERS

BACKGROUND OF THE INVENTION

This invention relates to benzhydryl fluoroalkyl ethers. Such compounds are useful, for example, as lubricating and dielectric fluids.

A wide variety of halogenated ethers have been disclosed in U.S. patents, for example U.S. Pat. Nos. 2,831,033, 2,409,274, 3,661,967, 2,564,214 and 2,702,825, as well as in foreign patents, for example French Pat. Nos. 1,463,398 and 1,501,630.

SUMMARY

An object of this invention is to provide novel ethers and a process for preparing same.

Upon further study of the specification and appended claims, further objects and advantages of this invention will become apparent to those skilled in the art.

To attain these objects, there are provided benzhydryl fluoroalkyl ethers of the formula

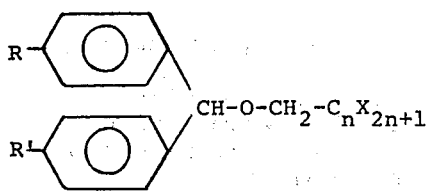

wherein X is F or H, at least one of the substituents X being F, $n$ is a whole number at least equal to 1, R and R' being identical or different represent H or Cl.

Owing to their physical chemical properties: high viscosity and high boiling point, these novel compounds are useful lubricants, hydraulic fluids and dielectric fluids.

The compounds of this invention are obtained by reacting benzhydrol or one of its derivatives which are halogenated on the benzene ring, with a halogenated aliphatic linear primary saturated alcohol.

DETAILED DISCUSSION

The benzhydrol and its derivatives have the formula:

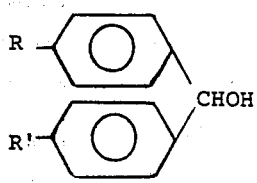

wherein R and R' are identical or different and are H or Cl. Suitable compounds include: benzhydrol (diphenylmethanol), parachloro diphenylmethanol and paradichloro diphenylmethanol. For purposes of simplification, the term "benzhydrol" is used herein to designate the different compounds having the formula as defined hereabove.

Aliphatic saturated linear primary alcohols suitable for preparing the ethers of the present invention are alcohols having the formula:

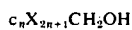

$C_nX_{2n+1}CH_2OH$ wherein X is F or H, at least one X being F, and $n$ is a whole number at least equal to 1, and preferably not more than 6 the particularly preferred range for $n$ being 1–4.

In the practice of the invention, the alcohols preferably used are the alcohols either partly or entirely substituted by fluorine on the carbon atoms which do not carry the alcohol function. Among suitable alcohols, fluorinated primary alcohols such as ethanol, 1-propanol, 1-butanol, 1-pentanol, 1-hexanol, 1-heptanol can be cited.

The reaction is performed by heating at about 50°C, a mixture constituted by the halogenated starting alcohol and an acidic dehydration agent. The halogenated starting alcohol is preliminarily dissolved in an aromatic solvent such as benzene, toluene, xylene and the like. The acid dehydration agent is for example concentrated sulfuric acid of hydrochloric acid and is used in a small quantity. Then the benzhydrol preliminarily dissolved in the same solvent as the halogenated alcohol is added to the reaction mixture. The reaction is achieved by heating and refluxing the reaction mixture with stirring for 1 to 7 hours.

According to the present invention, stoichiometric quantities of the fluorinated alcohol and of the benzhydrol can be used but preferably an excess of the fluorinated alcohol is used. Generally the amount of fluorinated alcohol ranges between 110 and 220 percent by weight and preferably 120 and 200% by weight of the molar theoretical quantity.

When the reaction is completed, the reaction mixture is treated with water. After decantation, the organic phase is washed successively with a weakly alkaline solution (for instance sodium bicarbonate) up to a pH of about 7 and finally with water. After decantation and drying (for example with calcium chloride), the aromatic solvent and the unreacted fluorinated alcohol are eliminated according to known techniques such as evaporation under vacuum, and the organic phase is distilled off under vacuum in order to obtain the aralkyl ether. According to the nature of starting reactants, aralkyl ethers yields can vary from 30 to 90 percent by weight based on the used benzhydrol.

Due to their physico-chemical properties: high viscosity and high boiling point, the ethers according to the present invention are useful lubricants, hydraulic fluids and dielectric fluids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In a reaction vessel (500ml) provided with a magnetic stirrer, a condenser and a dropping funnel, 0.5 mole (50g) of trifluoroethanol were introduced and dissolved in 50ml of dry benzene. Then 5ml of concentrated sulfuric acid were introduced: the mixture was stirred and heated by gradually raising the temperature to 50°C. Then, 0.25 mole (46g) of benzhydrol preliminarily dissolved in 70ml of benzene by heating, was slowly added to the reaction mixture. The mixture was stirred and refluxed for 6 hours.

After cooling, water was added to the reaction mixture. The acidic organic phase was neutralized with a sodium bicarbonate solution and washed with distilled water. After decantation and drying with calcium chloride the organic phase was evaporated by a water jet aspirator.

After distillation under vacuum (10mm Hg), there were obtained 50g of an oily yellowish product. An analytical study by vapor phase chromatography revealed that this product contained impurities. After redistillation under a vacuum of 10 mm Hg there were obtained 46g of 1-trifluoro-ethyl benzhydryl ether corresponding to a yield of 70 percent by weight based on the consumed benzhydrol. This ether was an amorphous white product having the following properties:

B.P. : 263°C
M.P. : 25 to 32°C
$n_D^{30}$ : 1.5070
N.M.R. analysis showed:
$\delta_{>CH-O}$ = 5.45 p.p.m. (singlet)
$\delta_{-CH_2-O}$ = 3.5 to 3.9 p.p.m. (quartet)
$\delta_{(C_6H_5)_2<}$ = 7.3 p.p.m. (main singlet of multiplet)

The data are consistent with and support the structure of the ether of formula:

$(C_6H_5)_2-CH-O-CH_2-CF_3$

EXAMPLE 2

Example 1 was repeated by using benzhydrol $(C_6H_5)_2$ CHOH and various halogenated alcohols. The obtained products are shown in Table 1.

EXAMPLE 3

In a reactor vessel equipped as described in Example 1, 44g (0.3 mole) of 2,2,3,3, tetrafluoropropanol-1 ($CF_2H-CF_2-CH_2OH$), 50ml of dry benzene and 5ml concentrated sulfuric acid were introduced. The reaction mixture was heated at 50°C, and a hot mixture of 54.6g (0.25 mole) of para-chlorobenzhydrol dissolved in 100ml of dry benzene was introduced. The reaction mixture was stirred at 50°C for 30 minutes; then the mixture was refluxed for 6 hours.

After cooling, the organic phase was neutralized at pH 7 with an alkaline solution, washed with water and dried with calcium chloride. Benzene was evaporated. The obtained oily product was distilled under vacuum, 53 grams of 1,1,2,2, tetrafluoropropyl para-chlorobenzhydryl ether were obtained corresponding to a yield of 63 percent by weight based on the consumed p-chlorobenzhydrol.

The obtained product had the following properties:
B.P. : 321°-322°C (decomposition)
$n_D^{20}$ : 1.5202
Viscosity at 20°C : 75 centistokes
Viscosity at 37.8°C : 19 centistokes
Viscosity at 98.9°C : 2.5 centistokes N.M.R. spectra of the 1,1,2,2, tetrafluoropropyl para-chlorobenzhydryl ether confirms its structure

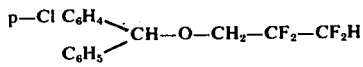

$\delta_{(C_6H_4-C_6H_5Cl-)}$ = 7.2 p.p.m. (main singlet of multiplet)
$\delta_{(>CH-O-)}$ = 5.3 p.p.m. (singlet)
$\delta_{(-CH_2-O-)}$ = 3.5 to 4 p.p.m. (triplet)
$\delta_{(HCF_2-CF_2-)}$ = 5.8 p.p.m. (triplet of triplets with a center at 5.8 p.p.m.)

N.M.R. spectrum achieved on $F_{19}$ confirms also this structure.

EXAMPLE 4

By using the mode of operation of Example 3, other ethers were obtained by reacting p-chlorobenzhydrol and 4,4'-dichlorobenzhydrol with various fluorinated alcohols. In Table 2, the results are set forth.

The nuclear magnetic resonance (NMR) spectra of the ethers obtained according to the present invention were achieved by using a 60 M.C. apparatus.

TABLE 1

| Starting fluorinated Alcohol | Obtained ether | Physical constants of the obtained ether | | NMR spectrum of the obtained ether | |
|---|---|---|---|---|---|
| $CF_3CF_2CH_2OH$ | $(C_6H_5)_2CHOCH_2CF_2CF_3$ | B.P. | : 262°C | $\delta_{(C_6H_5)_2<}$ | : 7.3 p.p.m. (main singlet of multiplet) |
| 2,2,3,3,3-pentafluoro-propanol-1 | 1,1,1,2,2-pentafluoropropyl benzhydryl ether | M.P. | ≈ −55°C | $\delta_{>CH-O}$ | : 5.4 p.p.m. (singlet) |
| | | $n_D^{20}$ | : 1.489 | | |
| | | Viscosity at 20°C : 13.44 centistokes | | $\delta_{(-CH_2-O-)}$ | : 3.5 at 4 p.p.m. (triplet) |
| $HCF_2CF_2CH_2OH$ | $(C_6H_5)_2CHOCH_2CF_2CF_2H$ | B.P. | : 298°C | $\delta_{(C_6H_5)_2<}$ | : 7.2 p.p.m. (main singlet multiplet) |
| 2,2,3,3-tetrafluoro-propanol-1 | 1,1,2,2-tetrafluoropropyl benzhydryl ether | $n_D^{20}$ | : 1.5060 | | |
| | | d20 | : 1.23478 | $\delta_{>CH-O-}$ | : 5.3 p.p.m. (singlet) |
| | | Viscosity at 20°C : 37.28 centistokes | | $\delta_{(CH_2-O-)}$ | : 3.4 at 3.9 p.p.m. (triplet) |
| | | | | $\delta_{(HCF_2-)}$ | : 5.8 p.p.m. (triplet of triplets with a center at 5.8 p.p.m.) |
| $CF_2H-(CF_2)_3-CH_2OH$ | $(C_6H_5)_2CH-O-(CH_2)(CF_2)_3-CF_2H$ | B.P. | : 270°C | $\delta_{(C_6H_5)_2<}$ | : 7.25 p.p.m. (main singlet of multiplet) |
| 2,2,3,3,4,4,5,5-octa-fluoropentanol-1 | | $n_D^{20}$ | : 1.473 | | |
| | 1,1,2,2,3,3,4,4-octafluoropentyl benzhydryl ether | Viscosity at 20°C : 48.64 centistokes | | $\delta_{>(CH-O-)}$ | : 5.4 p.p.m. (singlet) |
| | | | | $\delta_{(CH_2-O-)}$ | : 3.7 at 4 p.p.m. (triplet) |
| | | | | $\delta_{(-HCF_2)}$ | : 5.9 p.p.m. (triplet of triplets with a center at 5.9 p.p.m.) |

Table 2

| Starting fluorinated alcohol | Obtained ether | Physical constants of the obtained ether | NMR spectrum of the obtained ether | |
|---|---|---|---|---|
| CF₃CH₂OH 2,2,2-trifluoro-ethanol-1 | p-ClC₆H₄<br>⟩CH—OCH₂CF₃<br>C₆H₅<br>1,1,1-trifluoroethyl-para monochloro-benzhydryl ether | B.P.:306°C<br>n_D²⁰:1.5211<br>Viscosity at 20°C: 20 centistokes | $\delta_{(C_6H_5-)}$ = <br> $\delta_{>(CH-O-)}$ = <br> $\delta_{(CH_2-O-)}$ = | 7.2 p.p.m. (main singlet of a multiplet)<br>5.3 p.p.m. (singlet)<br>3.4 p.p.m. (quartet) at 3.8 p.p.m. |
| CF₃CH₂OH 2,2,2-trifluoro-ethanol-1 | p-ClC₆H₄<br>⟩CH—OCH₂CF₃<br>p-ClC₆H₄<br>1,1,1-trifluoroethyl-para-dichloro benzhydryl ether | M.P.:341–342°C (decomposition)<br>n_D²⁰:1.5333<br>d20:1.35111<br>Viscosity at 20°C: 52.73 centistokes | $\delta_{(C_6H_4Cl_2)}$< = <br> $\delta_{>(CH-O-)}$ = <br> $\delta_{(CH_2-O)}$ = | 7.2 p.p.m. (main<br>5.4 p.p.m. (singlet)<br>3.5 at 3.9 p.p.m. (quartet) |
| CF₂HCF₂CH₂OH 2,2,3,3 tetra-fluoro-propanol-1 | p-ClC₆H₄<br>⟩CH—OCH₂CF₂CF₂H<br>p-ClC₆H₄<br>1,1,2,2-tetrafluoropropyl-para dichloro benzhydryl ether | B.P.:147–155°C/1mm (decomposition) impure heavy oil<br>Viscosity at 20°C: 206 centistokes | NMR spectrum confirms the presence of radicals : (C₆H₄Cl)>(CHO)—and —(HCF₂), but the ether is impure. | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ether of the formula:

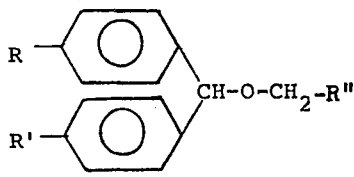

wherein R" is an alkyl of not more than 6 carbon atoms and has at least 3 fluorine atoms bonded thereto, R and R' being identical or different represent H or Cl.

2. An ether according to claim 1 wherein R" is an alkyl of not more than 4 carbon atoms.

3. An ether according to claim 1, wherein R and R' both represent H.

4. An ether according to claim 2, wherein R and R' both represent H.

5. An ether according to claim 1, wherein R is H and R' is Cl.

6. An ether according to claim 2, wherein R is H and R' is Cl.

7. An ether according to claim 1, wherein both R and R' represent Cl.

8. An ether according to claim 2, wherein both R and R' represent Cl.

9. (C₆H₅)₂—CH—O—CH₂—CF₃ according to claim 1.

10. (C₆H₅)₂—CH—O—CH₂—CF₂—CF₃ according to claim 1.

11. (C₆H₅)₂—CH—O—CH₂—CF₂—CF₂H according to claim 1.

12. (C₆H₅)₂—CH—O—CH₂—(CF₂)₃—CF₂H according to claim 1.

13.

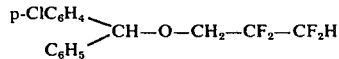

according to claim 1.

14.

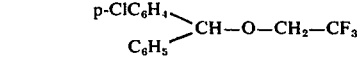

according to claim 1.

15.

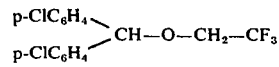

according to claim 1.

16.

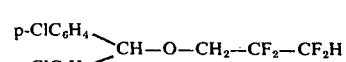

according to claim 1.

* * * * *